United States Patent [19]

Farnswoth, III

[11] Patent Number: 5,060,662
[45] Date of Patent: Oct. 29, 1991

[54] OPEN AIR BANDAGE

[76] Inventor: Kenneth F. Farnswoth, III, 605 W. Mill St., Ukiah, Calif. 95482

[21] Appl. No.: 549,262

[22] Filed: Jul. 6, 1990

[51] Int. Cl.$^5$ .................. A61F 13/00; A61F 15/00
[52] U.S. Cl. ............................. 128/888; 128/155; 128/887; 128/894
[58] Field of Search .............. 128/155, 887, 888, 893, 128/894, DIG. 20; 604/304, 307

[56] References Cited

U.S. PATENT DOCUMENTS

| | | |
|---|---|---|
| 802,190 | 10/1905 | Heineman . |
| 974,295 | 11/1910 | Pond . |
| 1,911,291 | 5/1933 | Reynolds . |
| 2,273,873 | 2/1942 | Klein . |
| 2,292,995 | 8/1942 | Greenwoll . |
| 2,399,545 | 4/1946 | Davis . |
| 2,585,691 | 2/1952 | Scholl ............................... 128/894 |
| 2,599,523 | 6/1952 | Dorr ................................. 128/894 |
| 2,807,262 | 9/1957 | Lew . |
| 2,858,830 | 11/1958 | Robins . |
| 3,143,099 | 8/1964 | Poole et al. . |
| 3,234,941 | 2/1966 | Tucker . |
| 3,298,366 | 1/1967 | Moore et al. . |
| 3,386,619 | 6/1968 | Douglas . |
| 3,416,524 | 12/1968 | Meier . |
| 3,528,416 | 9/1970 | Chamberlain ..................... 128/888 |
| 3,814,095 | 6/1974 | Lubens ............................. 604/307 |
| 3,888,247 | 6/1975 | Stenvall . |
| 3,927,669 | 12/1975 | Glatt . |
| 4,341,207 | 7/1982 | Steer et al. . |
| 4,360,015 | 11/1982 | Mayer . |
| 4,399,816 | 8/1983 | Spangler ........................... 128/888 |
| 4,413,621 | 11/1983 | McCracken et al. . |
| 4,559,949 | 12/1985 | Levine . |
| 4,600,001 | 7/1986 | Gilman . |
| 4,622,089 | 11/1986 | Lauritzen . |
| 4,649,909 | 3/1987 | Thompson . |

FOREIGN PATENT DOCUMENTS

| | | | |
|---|---|---|---|
| 269588 | 1/1914 | Fed. Rep. of Germany | 604/304 |
| 1303238 | 7/1962 | France | 128/888 |

Primary Examiner—David J. Isabella
Assistant Examiner—Paul Prebilic
Attorney, Agent, or Firm—Flehr, Hohbach, Test, Albritton & Herbert

[57] ABSTRACT

A bandage which is particularly suitable for use on large wounds such as skin grafts and burns. The bandage has a ring of pliant material adapted for engagement with the skin surrounding a wound, an absorbent material extending around the inner periphery of the ring of pliant material for collecting exudate from the wound, an adhesive on the lower side of the ring of pliant material for affixing the bandage to the skin, an air permeable member affixed to the upper side of the ring of pliant material and adapted to cover the area within the ring without touching the wound, and an outer protective layer overlying the air permeable member and having a plurality of openings through which air can pass.

3 Claims, 1 Drawing Sheet

OPEN AIR BANDAGE

This invention pertains generally to surgical dressings and bandages and, more particularly, to a bandage which can be used on relatively large wounds such as skin graft sites and burns.

It is in general an object of the invention to provide a new and improved bandage for use in the dressing of wounds.

Another object of the invention is to provide an bandage of the above character which is particularly suitable for use on relatively large wounds such as skin graft sites and burns.

These and other objects are achieved in accordance with the invention by providing a bandage having a ring of pliant material adapted for engagement with the skin surrounding a wound, an absorbent material extending around the inner periphery of the ring of pliant material for collecting exudate from the wound, an adhesive on the lower side of the ring of pliant material for affixing the bandage to the skin, an air permeable member affixed to the upper side of the ring of pliant material and adapted to cover the area within the ring without touching the wound, and an outer protective layer overlying the air permeable member and having a plurality of openings through which air can pass.

Figure 1:
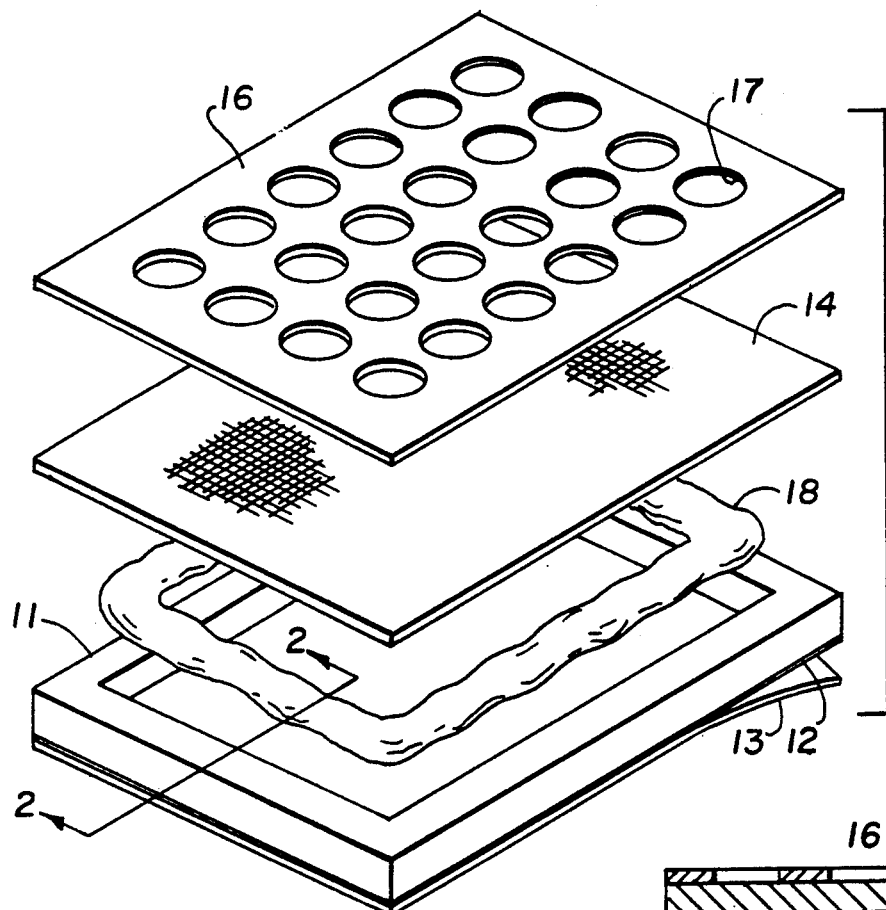
FIG. 1 is an exploded isometric view of one embodiment of a bandage according to the invention.
Figure 2:
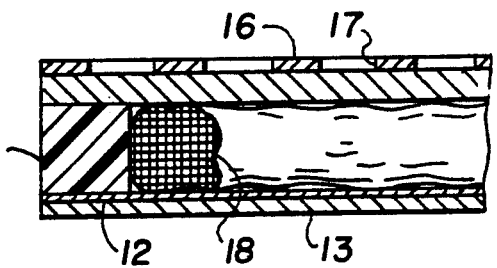
FIG. 2 is a cross-sectional view of the embodiment of FIG. 1.

As illustrated in FIG. 1, the bandage includes a generally rectangular ring 11 of pliant material, such as a flexible foam, which is adapted for engagement with the skin surrounding the site of the wound to be covered. The ring serves as a spacer which holds the rest of the bandage out of contact with the wound, and it typically has a thickness on the order of ⅛-½inch, depending upon the size of the area to be covered. The ring shown in the particular embodiment has a generally rectangular configuration, but it can have any other shape desired, e.g. circular or elliptical. A layer of adhesive 12 is provided on the lower surface of the ring for affixing the bandage to the skin, and a protective strip 13 covers the adhesive prior to use.

An air permeable member 14 is affixed to the upper side of ring 11 for covering the wound site in a spaced parallel relationship to the skin without touching the wound. This member is fabricated of a material such as nylon gauze through which air can pass, and it is spaced above the wound by a distance corresponding to the thickness of the ring.

An outer protective layer 16 overlies the air permeable member and has a plurality of relatively large openings 17 through which air can circulate. This layer can be fabricated of a material such as foam, cardboard, or a plastic film, and is affixed to the upper side of the air permeable member.

A ring 18 of absorbent material extends around the inner periphery of ring 11 for collecting exudate or fluids which drain from the wound. This ring is fabricated of an absorbent material such as cotton fibers or other cellulose material, and is conveniently formed as an elongatred strip of the absorbent material wrapped about and affixed to the inner periphery of the outer ring.

Figure 3:
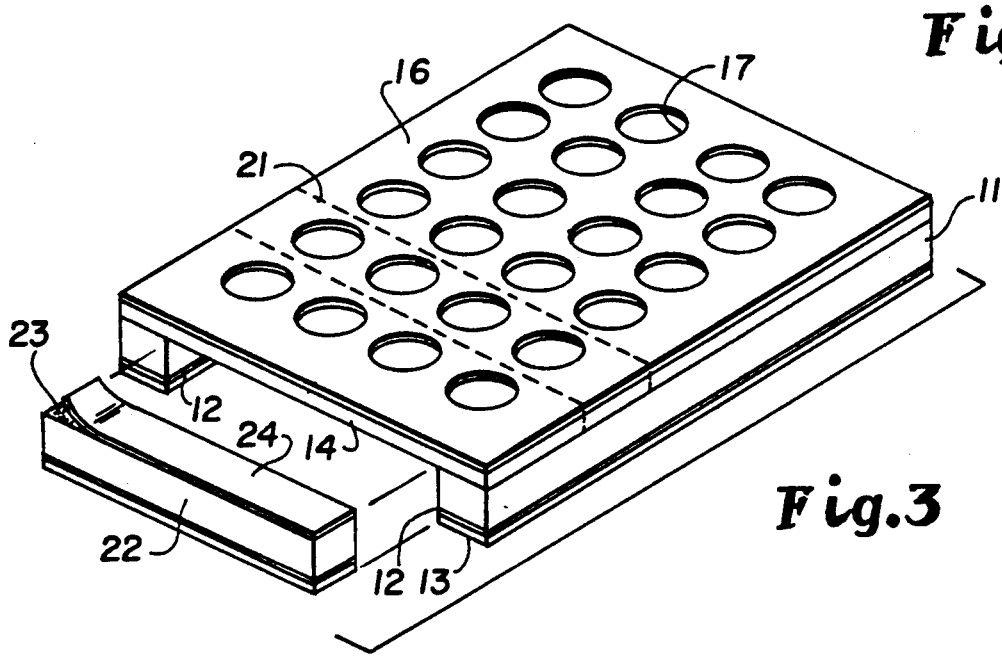
FIG. 3 is an isometric view of another embodiment of a bandage according to the invention.

In the embodiment illustrated in FIG. 3, ring 11, air permeable member 14 and protective layer 16 are formed with lines of perforations 21 which permit the bandage to be separated into sections for application to wounds of different sizes. In this embodiment, one side of ring 11 is formed as a separate piece 22 with adhesive 23 on its upper surface for attachment to the under side of air permeable member 14 along the edge of the section where the bandage is separated. A removable backing 24 covers the adhesive prior to use. In use, the bandage is torn to the desired size along one of the lines of perforations, backing 24 is removed, piece 22 is attached to the under side of the air permeable member to complete the ring, and the bandage is applied to the skin around the wound site. If an absorber for exudate from the wound is desired, a strip of absorbent material is placed around the inner periphery of the ring before the bandage is applied to the skin.

The bandage can be used in a variety of applications such as skin grafts, donor sites for skin grafts, burns, abrasions, and as a cover for an intravenous connection. It can also be utilized as a holder for a salve, ointment or other medication applied topically to the skin. It provides protection for a wound while permitting air to circulate and promote the healing of the wound. It also keeps the wound clean, alleviates discomfort, and permits clothing to be worn over the wound.

It is apparent from the foregoing that a new and improved bandage has been provided. While only certain presently preferred embodiments have been described in detail, as will be apparent to those familiar with the art, certain changes and modifications can be made without departing from the scope of the invention as defined by the following claims.

I claim:

1. A bandage comprising a ring of pliant material having upper and lower sides and being adapted for engagement with the skin surrounding a wound, an absorbent material extending around the inner periphery of the ring of pliant material for collecting exudate from the wound, an adhesive on the lower side of the ring of pliant material for affixing the bandage to the skin, an air permeable member affixed to the upper side of the ring of pliant material and adapted to cover the area within the ring without touching the wound, and an outer protective layer of pliant foam overlying the air permeable member and having a plurality of openings through which air can pass.

2. A bandage comprising a ring of pliant material having upper and lower sides and being adapted for engagement with the skin surrounding a wound, an adhesive on the lower side of the ring of pliant material for affixing the bandage to the skin, an air permeable member affixed to the upper side of the ring of pliant material and adapted to cover the area within the ring without touching the wound, and an outer protective layer of pliant foam overlying the air permeable member and having a plurality of openings through which air can pass.

3. A bandage comprising a ring of pliant material having upper and lower sides and being adapted for engagement with the skin surrounding a wound, a ring of absorbent material extending around the inner periphery of the ring of pliant material for collecting exudate from the wound, an adhesive on the lower side of the ring of pliant material for affixing the bandage to the skin, and a generally planar air permeable member affixed to the upper side of the ring of pliant material and adapted to cover the area within said ring of pliant material in spaced parallel relationship to the skin without touching the wound.

* * * * *